United States Patent [19]

Gittos

[11] Patent Number: 5,508,287
[45] Date of Patent: Apr. 16, 1996

[54] 2,6-METHANO-2H-QUINOLIZIN DERIVATIVE AS 5-$HT_3$-RECEPTOR ANTAGONIST

[75] Inventor: Maurice W. Gittos, Plobsheim, France

[73] Assignee: Merrell Pharmaceuticals Inc., Cincinnati, Ohio

[21] Appl. No.: 290,792

[22] PCT Filed: Feb. 3, 1993

[86] PCT No.: PCT/US93/00880

§ 371 Date: Aug. 16, 1994

§ 102(e) Date: Aug. 16, 1994

[87] PCT Pub. No.: WO93/17019

PCT Pub. Date: Sep. 2, 1993

[30] Foreign Application Priority Data

Feb. 24, 1992 [EP] European Pat. Off. ............ 92400474

[51] Int. Cl.$^6$ .................... C07D 471/18; C07D 221/00; A61K 31/435
[52] U.S. Cl. ............................................. 514/294; 546/79
[58] Field of Search ................................ 546/79; 514/294

[56] References Cited

FOREIGN PATENT DOCUMENTS

| | | |
|---|---|---|
| 0329932 | 8/1989 | European Pat. Off. . |
| 0450757 | 10/1991 | European Pat. Off. . |
| 0517984 | 12/1992 | European Pat. Off. . |
| 12569 | 11/1990 | WIPO . |

OTHER PUBLICATIONS

J. of Med. Chem. vol. 35, No. 2, pp. 310–319 (1992)—D. W. Robertson et al. "Zatosetron, a potent, selective, and long-acting 5$HT_3$ receptor antagonist: synthesis and structure-activity relationships".

*Primary Examiner*—Alan L. Rotman
*Attorney, Agent, or Firm*—Carolyn D. Moon

[57] ABSTRACT

This invention relates to 5-chloro-2,3-dihydro-2,2-dimethylbenzofuran-7-carboxylic acid-octahydro-3-hydroxy-2,6-methano-2H-quinolizin-8-yl ester (I), a novel 5-$HT_3$-receptor antagonist, its method of preparation, and to its end-use application in the treatment or radio- and chemo-therapeutically-induced nausea and vomiting, in the treatment or pain associated with migraine, in the treatment of cognitive disorders, in treating hallucinatory endogenous psychoses or the type manifested in patients suffering from schizophrenia and mania, for irritable bowel syndrome, and to combat drug abuse.

3 Claims, No Drawings

2,6-METHANO-2H-QUINOLIZIN DERIVATIVE AS 5-HT$_3$-RECEPTOR ANTAGONIST

CROSS REFERENCE

This application is a 371 of PCT/US93/00880 filed Feb. 3, 1993.

This invention relates to 5-chloro-2,3-dihydro-2,2 -dimethylbenzofuran-7-carboxylic acid-octahydro-3-hydroxy-2,6-methano-2H-quinolizin-8-yl ester, a novel 5-HT$_3$-receptor antagonist, its method of preparation, and to its end-use application in the treatment of conditions responsive to 5-HT$_3$ receptor antagonism such as radio- and chemotherapeutically-induced nausea and vomiting, the treatment of pain associated with migraine, in the treatment of cognitive disorders such as Alzheimer's Disease, the treatment of hallucinatory endogenous psychoses of the type manifested in patients suffering from schizophrenia and mania, the treatment of irritable or inflammatory bowel syndrome, or to combat drug abuse.

More specifically this invention relates to compounds of the formula

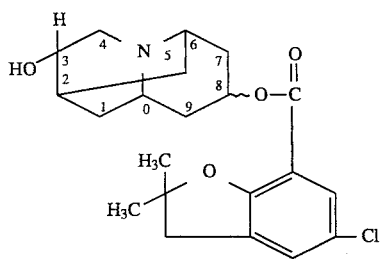

I its tautomers, stereo- and geometrical isomers, and mixtures thereof, and to the pharmaceutically acceptable salts thereof.

As used herein, the wavy line bonding the oxygen atom of the ester moiety to the 8-position of the octahydro-2,6-methano-2H-quinolizin moiety (hereinafter sometimes referred to as the methano bridged quinolizinyl moiety) indicates that the bonding may be in the endo (trans) or the exo (cis) configuration. The preferred configuration is endo. Preparation of such geometric isomers may be effected by the processes and techniques of U.S. Pat. No. 4,906,755 which is incorporated herein by reference. A chirality exists at the 3-position of the methano-bridged quinolizinyl moiety presenting d- or 1-isomers and racemate mixtures thereof. When desired resolution of said racemates may be effected by standard procedures and techniques well known in the art. The (+) enantiomer is preferred.

The pharmaceutically acceptable acid addition salts referred to above can be non-toxic salts with suitable acids such as those with inorganic acids, for example, hydrochloric, hydrobromic, nitric, sulfuric or phosphoric acids; or with organic acids such as organic carboxylic acids, for example, acetic, propionic, glycolic, maleic, hydroxymaleic, malic, tartaric, citric, salicylic, 2-acetyloxybenzoic, nicotinic or isonicotinic; or organic sulfonic acids, for example, methanesulfonic, ethanesulfonic, 2-hydroxyethanesulfonic, 4-toluenesulfonic or 2-naphthalenesulfonic.

The preparation of the compounds of the present invention may be illustrated by the following example.

EXAMPLE

5-CHLORO-2,3-DIHYDBO-2,2-DIMETHYLBENZOFURAN-7-CARBOXYLIC ACID TRANS-OCTAHYDRO-3-HYDROXY-2,6-METHANO-2H-QUINOLIZIN-8-YL ESTER

STEP A: Using triphosgene

5-Chloro-2,3-dihydro-2,2-dimethylbenzofuran-7-carboxylic acid trans-octahydro-3-oxo-2,6-methano-2H-quinolizin-8-yl ester A solution of triethylamine (1.79 g), 4-dimethylaminopyridine (1.09 g) and 5-chloro-2,3-dihydro-2,2-dimethylbenzofuran- 7-carboxylic acid (3.8 g) in dichloromethane (75 ml) was slowly added to a stirred solution of triphosgene (5.28 g) in dichloromethane (100 ml) at 0° C., nitrogen being continuously bubbled through the mixture. After the addition, the mixture was stirred at room temperature overnight under nitrogen, filtered and evaporated.

A suspension of the residue in anhydrous toluene was refluxed with a stirred suspension of hexahydro-8-hydroxy-2,6-methano-2H-quinolizin-3(4H)-one (3.25 g) overnight. The cooled solution was filtered, the toluene washed with aqueous potassium carbonate, dried over magnesium sulphate and evaporated to give a residue (4.8 g ) containing the title compound. It was then purified by partitioning between ethyl acetate (200 ml) and 1N methanesulphonic acid (40 ml). Basification of the separated methanesulphonic acid solution with a saturated aqueous solution of potassium carbonate gave a crystalline solid which was further purified by crystallization, e.g., from aqueous methanol or by silica gel chromatography to give a pure sample of the title compound.

Step A' (Alternate to Step A): Using trichloromethyl chloroformate

5-Chloro-2,3-dihydro-2,2-dimethylbenzofuran-7-carboxylic acid trans-octahydro-3-oxo-2,6-methano-2H-quinolizin-8-yl ester A solution of trichloromethyl chloroformate (1.76 g, 1.08 ml) in dichloromethane (10 ml) was added to a stirred solution of 5-chloro-2,3-dihydro-2,2-dimethylbenzofuran-7-carboxylic acid (2 g) and triethylamine (1.4 ml) in dichloromethane (30 ml) at 0° C. The mixture was stirred overnight at room temperature, washed with an ice cold saturated aqueous solution of ammonium chloride, dried over magnesium sulphate and evaporated to give an oil (2.2 g). A stirred mixture of the oil ((2.2 g), hexahydro-8-hydroxy-2,6-methano-2H-quinolizin-3(4)-one (1.6 g) and toluene (30 ml) was refluxed overnight. The cooled mixture was washed with a saturated aqueous solution of potassium carbonate and then four times with water to remove any unreacted hexahydroquinolizine one. Evaporation of the dried toluene solution (MgSO$_4$) gave a solid residue which was recrystallized from ethyl acetate/hexane to give the title compound (0.35 g).

STEP B:

5-Chloro-2,3-dihydro-2,2-dimethylbenzofuran-7-carboxylic acid trans-octahydro-3-hydroxy-2,6-methano-2H-quinolizin-8-yl ester Sodium borohydride (1.52 g) was slowly added to a stirred solution of 5-chloro-2,3-dihydro-2,2-dimethylbenzofuran-7-carboxylic acid trans-octahydro-3-oxo-2,6-methano-2H-quinolizin-8-yl ester (3.9 g) in ethanol (75 ml) at room temperature and the mixture stirred at room temperature overnight. The ethanol was evaporated, the residue dissolved in a mixture of water (20 ml) and 2N hydrochloric acid (20 ml), and the acidic solution almost immediately basified by the addition of an excess of a saturated solution of aqueous potassium carbonate. Extraction with a mixture of tetrahydrofuran-ethyl acetate (1.1) and evaporation of the dried extract gave the title compound. m.p.: 192°–193° C.

Conversion to the methane sulphonate salt was effected by the addition of one equivalent of an alcoholic solution of methanesulphonic acid and evaporation of the solvent.

The racemic mixture can be separated into its separate enantiomers by standard techniques.

The compounds of the present invention block the M receptors for 5-hydroxytryptamine (5HT) on afferent sensory neurons otherwise known as $5HT_3$-receptors. The activity of the compounds of this invention against the $5HT_3$-receptor can be assessed by determining their $pA_2$ values in the isolated rabbit heart as described by J. R. Fozard et al., Eur. J. Pharmacol. 59, 195–210 (1979). The in vivo $5HT_3$-receptor antagonist activity can be assessed by measurement of the effect of the compound on the Von Bezold-Jarisch reflex induced by 5HT injected intravenously into the rat (see Paintal A. S., Physiol. Rev. 53, 159–227 (1973); J. R. Fozard, Naunyn-Schmiedeberg's Arch. Pharmacol. 326, 36–44 (1984).

Using the foregoing standard procedures, as well as other standard procedures recognized to illustrate $5HT_3$-receptor antagonist activity for the above-stated end-use applications, as well as by comparison with other $5HT_3$-receptor antagonists known to be useful for such purposes, the compounds of this invention may be utilized in a variety of treatments.

Generally, the compounds of the present invention are useful in treating conditions responsive to $5$-$HT_3$ receptor antagonism. Examples of conditions responsive to $5$-$T_3$ receptor antagonism are well known to those skilled in the art. Some examples of these conditions are treating anxiety, psychosis, glaucoma and for stimulating gastric motility (U.S. Pat. No. 5,011,846), treatment of panic disorders and/or agoraphobia or obsessive compulsive disorders (Patent No. EP 422,154); treatment of autism or other disorder originating in childhood in which there is mental retardation (Patent No. EP 450,757); treatment of cognitive disorders such as Alzheimer's Disease (U.S. patent application Ser. No. 806,987); production of orexiogenic effect (U.S. patent application Ser. No. 742,951); serotonin-induced nasal disorders, rhinitis or impaired approach-oriented behavior in stressful situations or for increasing vigilance (Patent No. GB 2,193,633); relief or prevention of withdrawal syndrome resulting from addiction to and/or for the suppression of dependence on a drug or substance (Patent No. EP 279,114 and GB 2,206,788); treatment of lung embolism (Patent No. GB 2,231,265); treatment of cough and/or bronchoconstriction (Patent No. EP 340,270); treatment of nausea, bradycardia, and/or hypotension associated with myocardial instability (Patent No. WO91/09593); treatment of urinary incontinence (Patent No. EP 467,365); and combination therapy with ACE inhibitors (Patent No. EP 477,625 and EP 477,624), with 3-[2-(dimethylamino)ethyl]-N-methyl-1H-indole-5-methanesulphonamide (Patent No. EP 433,043); and histamine $H_2$-receptor antagonist (Patent No. EP 275,669). All of the foregoing are incorporated herein by reference.

Preferred uses for the compounds of the present invention include the treatment of nausea and vomiting, particularly radio- and chemo-therapeutically induced in those patients being treated for cancer, in the treatment of pain associated with migraine and neuralgia, in the treatment of cognitive dysfunctions such as memory and learning disorders as well as dysfunctions in selective attention, in the treatment of hallucinatory endogenous psychoses of the type manifested in patients suffering from schizophrenia and mania, for the treatment of irritable or inflammatory bowel syndrome, as well as to be useful in combating drug abuse.

Doses administered to patients are within the range of about 0.01 to about 10 mg per kilogram of body weight, with 0.01 to 1 mg per kilogram of body weight being preferred for parenteral administration and 0.25 to 1 mg per kilogram of body weight upon enteral administration. Of course, the dosage required for the treatment of the foregoing disease states will depend upon such factors as the severity and stage of the particular disease, the age and condition of the patients as such other normal factors taken into consideration by the attending diagnostician.

The term "patient" means warm-blooded animals such as rats, mice, dogs, cats, guinea pigs, primates and humans. The term "treat" means to prevent or alleviate the patient's disease or condition.

The compounds of Formula (I) can be administered in various manners to achieve the desired effect. For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula (I) can be tableted with conventional tablet bases such as lactose, sucrose, and cornstarch in combination with binders, such as acacia, cornstarch, or gelatin, disintegrating agents such as potato starch or algenic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc. as are known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894 incorporated herein. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636 incorporated herein. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

Specific formulations of the present invention are prepared in a manner well known per se in the pharmaceutical art and usually comprise one or more active compounds of the invention in admixture or otherwise in association with a pharmaceutically acceptable carrier or diluent therefor. The active ingredient will usually be mixed with a carrier, or diluted by a diluent, or enclosed or encapsulated in a capsule, sachet, cachet, paper or other container. A carrier or diluent may be solid, semisolid or liquid material which serves as a vehicle, excipient or medium for the active ingredient. Suitable carriers or diluents are well known per se. See Remington's Pharmaceutical Sciences, Mack Publishing Company, Easton, Pa., incorporated herein, for a description of the preparation of such formulations.

What is claimed is:

1. A compound of the formula

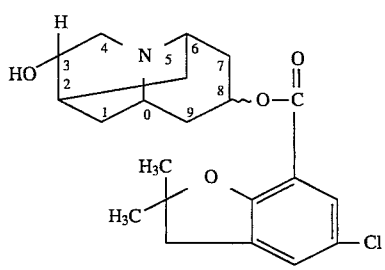

its tautomers, stereo- and geometrical isomers, and mixtures thereof, or the pharmaceutically acceptable salts thereof.

2. A pharmaceutical composition comprising an effective amount of the compound of claim 1 and a pharmaceutically acceptable carrier.

3. A method of treating a patient in need of such therapy with an effective amount of the compound according to Claim 1 for treating nausea and vomiting, treating migraine, treating cognitive disorders, or treating irritable or inflammatory bowel syndrome.

\* \* \* \* \*